(12) United States Patent
Segal et al.

(10) Patent No.: US 8,517,732 B2
(45) Date of Patent: Aug. 27, 2013

(54) DENTAL MATRIX CLAMP

(75) Inventors: Alan Julian Segal, Cheshire (GB); Christopher James Thorp, Manchester (GB)

(73) Assignee: Astek Innovations Limited, Cheshire (GB)

( * ) Notice: Subject to any disclaimer, the term of this patent is extended or adjusted under 35 U.S.C. 154(b) by 0 days.

(21) Appl. No.: 13/127,062

(22) PCT Filed: Nov. 2, 2009

(86) PCT No.: PCT/GB2009/002587
§ 371 (c)(1),
(2), (4) Date: May 2, 2011

(87) PCT Pub. No.: WO2010/061161
PCT Pub. Date: Jun. 3, 2010

(65) Prior Publication Data
US 2011/0244421 A1    Oct. 6, 2011

(30) Foreign Application Priority Data
Nov. 1, 2008    (GB) .................................. 0820074.3

(51) Int. Cl.
*A61C 5/04*    (2006.01)
(52) U.S. Cl.
USPC ............................................ 433/155; 433/39
(58) Field of Classification Search
USPC ............... 433/39, 136–141, 152–162; 269/3, 269/6, 131; 81/3.43, 64, 65; 279/95, 96
See application file for complete search history.

(56) References Cited

U.S. PATENT DOCUMENTS

| | | | | | |
|---|---|---|---|---|---|
| 767,852 | A | * | 8/1904 | Tibbetts | 433/39 |
| 1,400,456 | A | * | 12/1921 | Petrak | 81/64 |
| 1,512,014 | A | * | 10/1924 | Bryar | 81/65 |
| 1,726,862 | A | * | 9/1929 | Schustarich | 81/3.43 |
| 2,367,439 | A | * | 1/1945 | Samphere | 433/155 |
| 2,439,703 | A | * | 4/1948 | Tofflemire | 433/155 |
| 2,687,573 | A | * | 8/1954 | Stone | 433/155 |
| 3,842,505 | A | | 10/1974 | Eames | |
| 4,532,833 | A | * | 8/1985 | Downs | 81/64 |
| 5,342,197 | A | * | 8/1994 | Stein et al. | 433/155 |
| 5,440,955 | A | * | 8/1995 | Freeland | 81/64 |
| 5,592,860 | A | * | 1/1997 | Woodsum | 81/180.1 |
| 6,520,052 | B1 | * | 2/2003 | Saunders et al. | 81/64 |
| 2006/0112792 | A1 | * | 6/2006 | Ping | 81/64 |

OTHER PUBLICATIONS

International Search Report for corresponding application No. PCT/GB2009/002587 dated Mar. 22, 2010.

* cited by examiner

*Primary Examiner* — Yogesh Patel
(74) *Attorney, Agent, or Firm* — Renner, Otto, Boisselle & Sklar, LLP

(57) ABSTRACT

A dental matrix clamp includes an elongate body and a matrix band mountable relative to the body so as to form a loop projecting at one end of the body. The clamp has a tensioning device operable on the band to tighten the loop, and a deflector member which engages the band to provide an inclined conformation thereto. The deflector member is adjustable transversely across the band between opposite positions at which it bears against opposite peripheral portions of the band. The clamp is a hand-held device used in dentistry to clamp a band around a tooth for retention and molding of filling material.

17 Claims, 4 Drawing Sheets

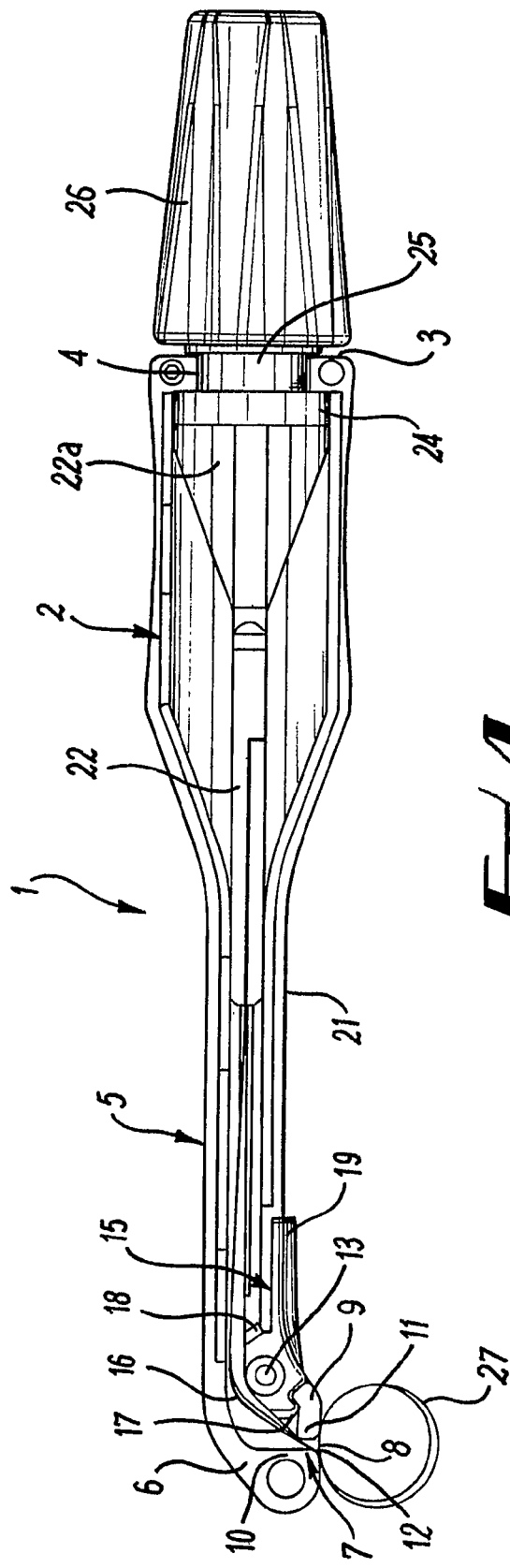

DENTAL MATRIX CLAMP

Figure 1:
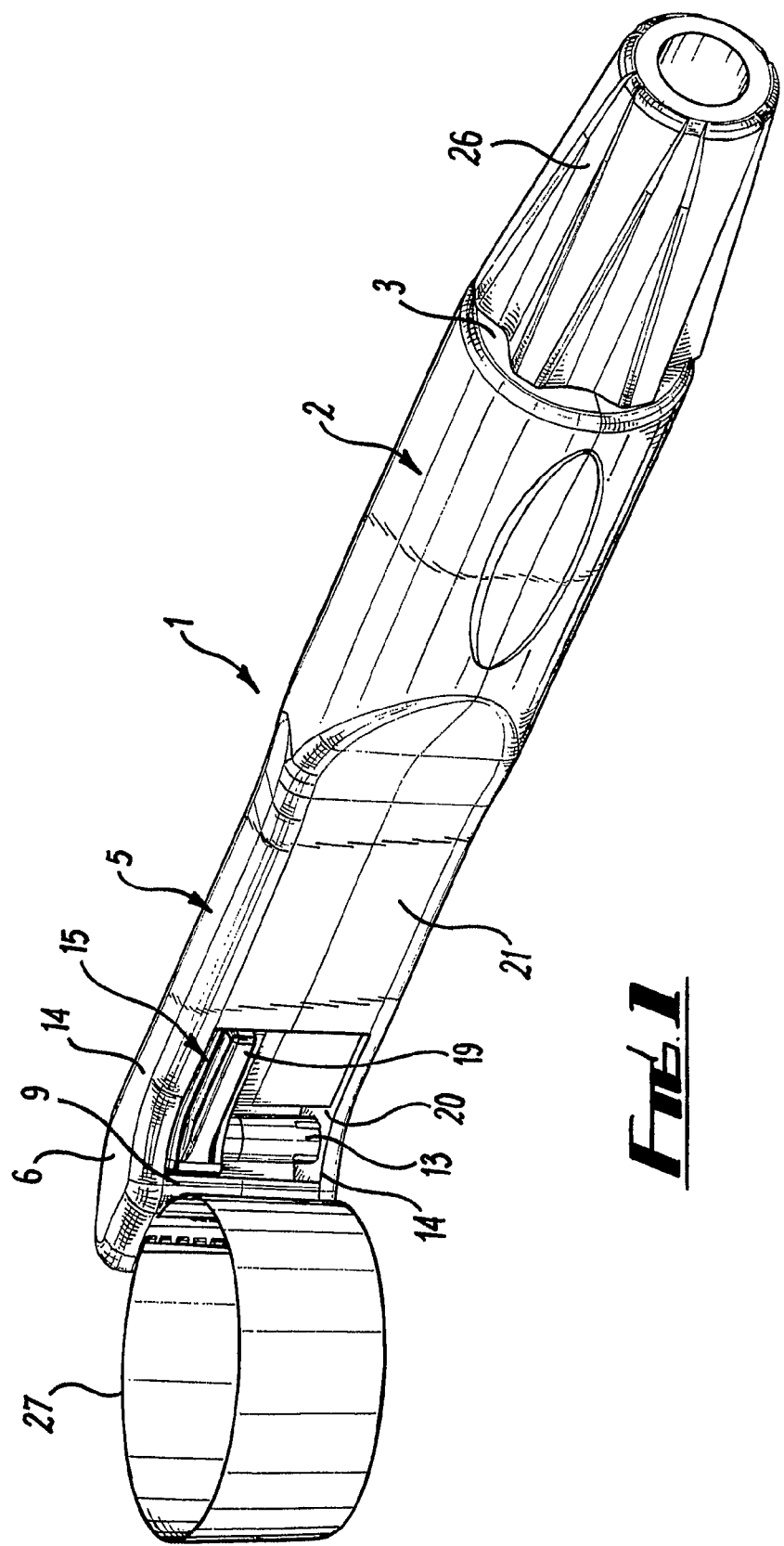

This application is a national phase of International Application No. PCT/GB2009/002587 filed Nov. 2, 2009 and published in the English language.

This invention relates to a dental matrix clamp, that is, a hand-held device used in dentistry to clamp a matrix band around a tooth to help retain and mould filling material in a side surface of the tooth.

A well known dental matrix clamp is the so-called Siqveland clamp described in GB 608107. This has an elongate metal body with a matrix band shaped into a loop mounted at one end of the body. The loop can be pulled tight around a tooth by adjusting a nut on a threaded rod connected to one end of the band. The band is an elongate metal strip with parallel straight long side edges and it therefore tends to adopt a cylindrical shape in the loop. In order to accommodate the typically inclined, generally conical, shape of tooth surfaces the band is provided with a clip which fits around, and holds together, opposite runs of the band adjacent the loop. The clip can be tilted so as to cause the loop to adopt a generally conical shape. The clip can be tilted in opposite directions to accommodate usage of the clamp with the loop at the left side of the clamp body, or, when turned over, with the loop at the right side. This allows the smooth-surfaced central part of the loop to be presented to either side of the tooth as required.

The Siqveland clamp can be inconvenient to use, because the clip has to be held manually in its tilted position. For avoidance of contamination problems, the band can be removed after use and replaced. However, the complexity of the fixing is such that this cannot be done quickly and easily.

Another known clamp is that described in U.S. Pat. No. 5,055,045. This also has an elongate body with a matrix band providing a loop at one end of the body; and an adjustment nut engageable with a threaded rod connected to the band is provided for tightening the loop. The band may be shaped e.g. with parallel long side edges which have a shallow V- or wing-shape so that one half of the band is at a small angle to the other half, whereby the loop naturally adopts a generally conical shape. The body is made as a relatively inexpensive plastics moulding and the entire clamp, with the matrix band, is intended to be discarded and replaced after use. To accommodate left and right hand use, the clamp has a pivot head which can be adjusted so that the loop projects either to the left or to the right with the clamp the same way up. This is convenient to use but the pivot head lacks the simplicity of the Siqveland clip and can be complicated and relatively expensive to manufacture.

An object of the present invention is to provide a dental matrix clamp which is convenient to use and which is of simple construction and of relatively inexpensive manufacture whereby it is suited to disposal and replacement after use.

According to the invention therefore there is provided a dental matrix clamp comprising an elongate body, a matrix band mountable relative to the body so as to form a loop projecting at one end of the body, a tensioning device operable on the band to tighten the loop, and a deflector member engageable with the band to impart an inclined conformation thereto, the deflector member being adjustable transversely across the band between opposite positions at which it bears respectively against opposite peripheral portions of the band.

With this arrangement, as the loop is tightened, an inclination can be imparted thereto in so far as that peripheral portion which is engaged by the deflector member is deflected differently from the opposite peripheral portion. By selection of the peripheral portion for engagement with the deflector member, the direction of inclination can be selected. This can enable the clamp to be used either way up whilst presenting the same direction of inclination. By reliance on the transversely movable deflector member to adjust direction of inclination, the clamp can be of simple construction so that it can be manufactured relatively inexpensively, particularly from plastics materials, and is therefore suited to disposal and replacement after use.

The transversely movable deflector member can be readily constructed for ease of use. Preferably a retention arrangement is provided to hold the member in each adjusted position so that it does not have to be retained manually. This may take any suitable form. Snap-fit connections may be provided. Alternatively, a simple friction engagement may be used.

The member may be slidable along a straight path transversely to the length of the band and generally parallel to its face. Other arrangements are however also possible.

The deflector member may bear exclusively on the selected peripheral portion of the band on one or both runs of the band externally of the loop. Other arrangements are also possible and thus, the member may bear on the inner side of the or each run. The effect of the deflector member is preferably to provide a longer path of travel for the selected peripheral portion of the loop, when tightened, relative to the opposite peripheral portion and/or to frictionally engage and restrict the rate of movement of the selected peripheral portion when tightened.

The deflector member may have a curved surface, such as a part-cylindrical surface for engagement with the band.

Most preferably, the loop projects at one side of the clamp body so that it can be used as a left hand or right hand loop depending on which way up the body is used.

Preferably the inclination of the loop produced by the effect of the deflector member is generally conical; and the band may have straight parallel long edges. Other arrangement are however also possible.

An alternative band may have a narrowed section in which the section of the band that that projects from the body and which forms the loop is narrower than the sections of the band which are mounted upon the body.

The protruding section may be outwardly curved across its width so that it can conform more to the shape of the tooth around which the clamp is to be arranged.

The band may be a metal band or may be formed from plastic. Suitable plastics may include polyester film (e.g. Mylar), and in particular transparent plastic films which would allow the user to see exactly where the band is place in relation to the tooth concerned. Additionally, when using composite filling materials which are set using a UV curing light the use of a transparent material allows for transmission of the UV light.

Any other suitable material can be used to form the band.

The tensioning device may comprise a screw member connected to one end or both ends of the band and a nut engageable with the screw member, whereby rotation of the nut relative to the screw member causes the screw member to move axially along the clamp body. The nut may be manually rotatable and may be captive axially relative to the body whereby the screw member moves axially through the nut.

The clamp body may be of elongate tubular form. The aforesaid manually rotatable nut may be at one end part thereof, which may be a rearward end part.

The body may have an end part which may be a forward end part with a neck portion through which the loop of the band projects externally of the body. This neck portion may be bounded by opposite guide members, such as body structures with curved surfaces. The said deflector member may be provided rearwardly of such guide members or may be incorporated in one such member. The deflector member may be slidably mounted on a pin or the like. The pin may be of circular cross-section, and the deflector member may have a part cylindrical deflector surface particularly coaxial with the pin. Alternatively, the deflector member may have a part cylindrical deflector surface which is offset such that it is not completely coaxial with the pin.

The body and the deflector member and the tensioning device may be wholly or substantially wholly formed from plastics material.

Figure 2:
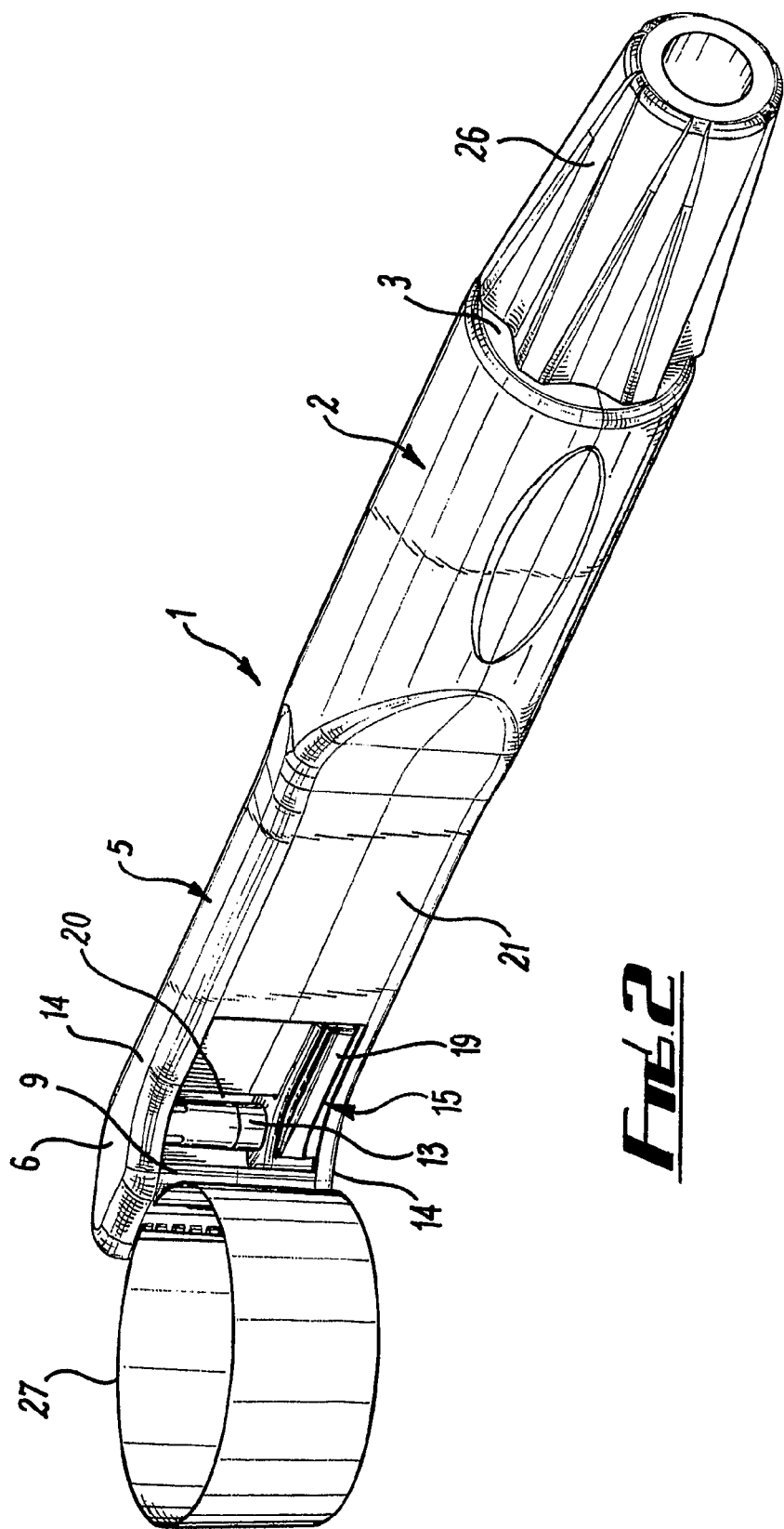
Figure 3:
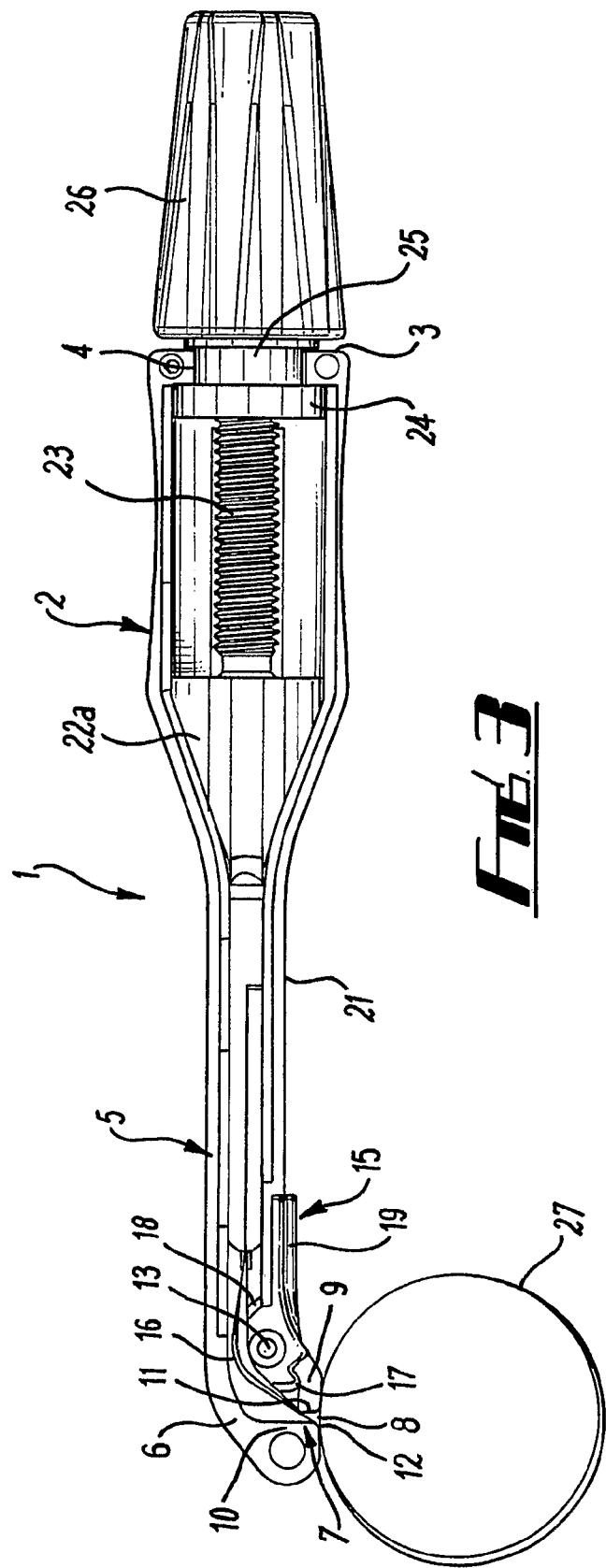

The invention will now be described further by way of example only and with reference to the accompanying drawings in which:

FIGS. 1 and 2 are side perspective views of one form of a dental matrix clamp in opposite adjustment positions; and FIGS. 3 and 4 are axial sectional views of the clamp of FIGS. 1 and 2 in different tightening positions of the band.

Referring to the drawings, there is shown a dental matrix clamp having an elongate tubular moulded plastics body 1. The body has a generally cylindrical rear part 2 which terminates at the rear end with an end wall 3 with a central circular opening 4. The body 1 tapers from the cylindrical rear part 2 towards the opposite front end and has a generally rectangular strip-shaped forward end part 5 with a leading end region 6 which is inclined to one side and terminates in a narrow neck portion 7 with a slot-shaped opening 8 extending at right angles to the longitudinal axis of the body 1.

The opening 8 of the neck portion 7 is bounded by opposed transverse body structures 9, 10 with parallel curved edges 11, 12 respectively at the forward and rearward sides. Rearwardly and inwardly of the rearward edge 11 there is a fixed cylindrical pin 13 parallel to the edges 11, 12. The edges 11, 12 and the pin 13 run between top and bottom narrow walls 14 of the forward end part 5 of the body 1.

Slidably mounted on the pin 13 is a short deflector member 15, its length being a minor proportion of the length of the pin 13. The member 15 has, at its inner side a part cylindrical surface 16 coaxial with the pin 13. At its outer side the member has diametrically opposite steps 17, 18 and an elongate rib 19 extending rearwardly longitudinally of the body 1. This rib 19 projects through an opening 20 in the adjacent side wall 21 of the forward part 5 of the body 1. The forward step 17 of the member 15 engages the body structure 9 providing the rearward bounding edge 11 of the neck portion 7. The rearward step 18 and the rib 19 engage opposite sides of an adjacent edge region of the body side wall 21 at the opening 20. The member 15 is slidably mounted on the pin 13 so it can be moved between opposite ends thereof, as shown respectively in FIGS. 1 and 2. The engagement of the steps 17, 18 and the rib 19 with the body structure 9 and the body side wall 21 provide frictional retainment so that the member 15 is retained in position on the pin 13 and can be moved only by application of manual pressure to the rib 19 in the axial direction of the pin 13.

Within the body 1 rearward of the member 15 there is a slidably mounted a strip member 22 extending axially along the body 1. The forward end of the strip member 22 is formed in two side-by-side parts which snap-fit together. The rearward end is connected axially, via a guide piston 22a, to a screw member 23 which engages and extends through a nut 24 within the rearward body part 2 internally of the open end wall 3 of the body 1, such nut 24 being of greater diameter than the opening 4 in the end wall 3. The nut 24 has an integral small diameter neck part 25 which extends through the opening 4 in the end wall 3 and is formed integrally with an external hollow end cap 26. The arrangement is such that manual rotation of the end cap 26 causes the screw member 23 to move axially into or out of the end cap 26, guided by sliding of the piston 22a in the cylindrical end part 2, the two part strip member 22 thereby also being caused to move axially.

A matrix band 27 which has straight parallel long side edges is mounted on the body 1. The band 27 may be formed from springy flexible metal or other similar material. The width of the band 27 is generally equal to the length of the pin 13.

The body 1, including the body structures 9, 10 and the pin 13 is formed in top and bottom snap fit parts. Alternatively, the body structures 9, 10 can be joined together using ultrasonic welding. Before assembly of these parts, the matrix band 27 is attached to the body with the members 22, 23 and the cap 26.

As shown, the two end regions of the band 27 are clamped between the two parts of the strip member 22. The remainder of the band extends through the neck portion 7 between the curved edges 11, 12 so as to form a circular loop externally of the body 1 at one side thereof. Between the neck portion 7 and the strip member 22 the opposite contacting runs of the band extend over the pin 13 and the part cylindrical surface 16 of the deflector member 15.

With the body 1 assembled and the matrix band, the members 22, 23 and the cap 26 fitted, rotation of the end cap 26 can be effected to tighten the loop, from the arrangement of FIG. 3, to that of FIG. 4, by drawing the strip member 22 and the attached end portions of the band 27 longitudinally along the body 1. With the deflector member 15 in the upper position as shown in FIG. 1, tightening of the loop causes the part cylindrical surface 16 to bear on the upper peripheral portion of the band 27 whereby the band 27 moves along a longer path at the top than at the bottom. It therefore adopts a generally conical conformation with the smaller diameter uppermost. This is because the cylindrical surface 16 of the member 15 provides a longer path than the pin 13. As shown in FIG. 2, with the member 15 at the bottom, the generally conical conformation is reversed with the smaller diameter lowermost.

The matrix clamp is used to retain and mould filler material in the side of a tooth by clamping the loop of the band 27 tightly round the tooth with the loop of the band 27 conically shaped with the smaller diameter lowermost. By selecting the position of the deflector member 15, the clamp can be arranged with the loop at the left hand or right hand side as required, in each case the smaller diameter of the loop being lowermost.

After use, the cap 26 is counter-rotated to release the loop, and the clamp is removed from the tooth for disposal.

The slidable, frictionally-retained deflector member 15 facilitates convenience of use and enables simple, relatively inexpensive manufacture, suited to disposal and replacement of the entire clamp and band.

It is of course to be understood that the invention is not intended to be restricted to the details of the above embodiment which are described by way of example only.

The invention claimed is:

1. A dental matrix clamp comprising an elongate body, an attachment structure on the body for mounting a matrix band to the body so as to form a loop projecting at one end of the body, a tensioning device carried by the body and operable on the band when mounted to the body to tighten the loop, and a single deflector member mounted to the body and engageable with the band when mounted to the body to impart an inclined conformation to the band, the deflector member being adjustable transversely across the band between opposite positions of the deflector member at which the deflector member bears respectively against opposite peripheral portions of the band, and the defector member is translatable along a straight path transversely to a longitudinal direction of the body.

2. The dental matrix clamp according to claim 1, wherein a retention arrangement is provided to hold the deflector member in adjusted positions so that the deflector member does not have to be retained manually.

3. The dental matrix clamp according to claim 1, wherein the deflector member is positioned so at to bear exclusively on a selected peripheral portion of the matrix band on one or both runs of said band externally of the loop.

4. The dental matrix clamp according to claim 3, wherein the deflector member bears on an inner side of said one or both runs.

5. The dental matrix clamp according to claim 1, wherein the deflector member has a curved surface for engagement with the matrix band.

6. The dental matrix clamp according to claim 5, wherein the curved surface is a part-cylindrical surface.

7. The dental matrix clamp according to claim 1, wherein the loop projects at one side of the clamp body so that the loop can be used as a left hand or right hand loop depending on which way up the body is used.

8. The dental matrix clamp according to claim 1, wherein the inclination of the loop produced by the effect of the deflector member is conical.

9. The dental matrix clamp according to claim 1, wherein the band has straight parallel long edges or wherein the band has a narrowed section such that the section of the band that projects from the body and which forms the loop is narrower than the sections of the band which are mounted upon the body.

10. The dental matrix clamp according to claim 1, wherein the band is outwardly curved across a width of the band.

11. The dental matrix clamp according to claim 1, wherein the tensioning device comprises a screw member connectable to one end or both ends of the band and a nut engageable with the screw member, whereby rotation of the nut relative to the screw member causes the screw member to move axially along the clamp body.

12. The dental matrix clamp according to claim 1, wherein the clamp body is of elongate tubular form.

13. The dental matrix clamp according to claim 1, wherein the body has an end part which is a forward end part with a neck portion bounded by opposite guide members through which the loop of the band projects externally of the body.

14. The dental matrix clamp according to claim 13, wherein the deflector member is provided rearwardly of said guide members.

15. The dental matrix clamp according to claim 13, wherein the deflector member is incorporated in one of the guide members.

16. The dental matrix clamp according to claim 1, wherein the deflector member is slidably mounted on a pin supported on the body.

17. The dental matrix clamp according to claim 1, further comprising the matrix band.

\* \* \* \* \*